United States Patent [19]
Liotta

[11] Patent Number: 5,456,715
[45] Date of Patent: Oct. 10, 1995

[54] IMPLANTABLE MECHANICAL SYSTEM FOR ASSISTING BLOOD CIRCULATION

[76] Inventor: Domingo S. Liotta, 3 de Febrero N° 2025, Buenos Aires, Argentina

[21] Appl. No.: 116,854

[22] Filed: Sep. 7, 1993

[30] Foreign Application Priority Data

May 21, 1993 [AR] Argentina ................................. 324900

[51] Int. Cl.$^6$ .................................................. A61M 1/12
[52] U.S. Cl. ................................................. 623/3; 600/16
[58] Field of Search ................................. 623/3, 24–26; 600/16–18

[56] References Cited

U.S. PATENT DOCUMENTS

| | | | |
|---|---|---|---|
| 5,318,501 | 6/1994 | Lee et al. | 600/16 |
| 5,344,385 | 9/1994 | Buck et al. | 600/16 |
| 5,397,349 | 3/1995 | Kolff et al. | 623/3 |

FOREIGN PATENT DOCUMENTS 0827070  5/1981  U.S.S.R. .................................... 623/3

OTHER PUBLICATIONS

Kimoto et al., Trans. Amer. Soc. Artif., Int. Organs, vol. X, 1964, pp. 66–67.
Kusseron et al., Trans. Amer. Soc., Artif Int. Organs, vol. X, 1964, pp. 74–78.
Novoa et al., Trans. Am. Soc. Artif. Intern. Organs, vol. XXXV, 1989, pp. 408–411.
Ugolini, "Skeletal Muscle for Artificial Heart Drive: Theory and in Vivo Experiments" (In Chiu: *Biomechanical Cardiac Assist*), pp. 193–210 (1986).

*Primary Examiner*—David H. Willse
*Attorney, Agent, or Firm*—Bachman & LaPointe

[57] ABSTRACT

Implantable mechanical system for assisting blood circulation using a blood circulation pump and wherein the system, being actuated by the power produced by the linear contraction of the skeletal muscle, comprises for its two-phase application: a combined prosthesis defining the bio-mechanical coupling between the skeletal muscle and the implantable mechanical system; a muscle action force multiplier transmitting force through a lever system driving compression plates of the blood chamber formed into the pump; the biomechanical coupling, the force multiplier and the lever system forming a functional unit interconnected by means of lead wires for transmiting movement; the system further comprising a device for measuring force and the displacement of the skeletal muscle driving the pump, during the electro-stimulation period through the system.

11 Claims, 6 Drawing Sheets

IMPLANTABLE MECHANICAL SYSTEM FOR ASSISTING BLOOD CIRCULATION

FIELD OF THE INVENTION

The instant invention relates to a muscle-powered implantable mechanical system for circulatory blood pumps providing a combination of means constituting a prosthesis powered by the skeletal muscle of the patient, for an implantable pump for assisting in chronic refractory heart failure.

BACKGROUND OF THE INVENTION—PRIOR ART

Treatment of end-stage chronic heart failure (CHF) is still a major challenge for physicians. This is the reason why scientists all over the world have been devoted for many years to the development of mechanical aid systems for blood circulation. Thus, in 1960 Kolff and coworkers, Liotta and coworkers and other researchers developed a series of devices for managing acute heart failure.

On Jul. 18, 1963, for the first time, Liotta et al employed a left ventricular assisting device for the treatment of a patient with acute cardiac disfunction during the post-operative period.

On Apr. 4, 1969, and for the first time in the medicine history, Cooley, Liotta et al implanted a total artificial heart in a patient, thus bridging the two-stage cardiac transplantation.

This technique expanded worldwide and was then employed by a large number of clinical centers; such that it may be affirmed that mechanical devices for aiding blood circulation, used as a bridge in cardiac transplantation are at present a general medical practice.

However, the main challenge of modern cardiology: the management of end-stage chronic heart failure (CHF) remains unsolved.

The mortality among CHF patients is reported to range between 10% and 20% a year; i.e. 200,000–400,000 deaths a year are caused by CHF in the United States.

On the other hand, if worldwide deaths are considered, due to the same causes, the number of deaths may range from 1,000,000 to 2,000,000 per year.

Also, there are regions in which additional negative factors area added to these diseases.

This is the case of South America, in which chagasic oardiomyopathy patients due to South American Trypnosomiasis (Chagas disease), cause that from 18 to 18 million people worldwide are likely to be infected by Trypanosoma Cruzi. 30% to 40% of those persons infected will ultimately have some degree of cardiac involvement.

In Argentina, from 250.000 to 400,000 patients suffer from chagasic oardiomyopathy. Chagasic patients cannot be selected for cardiac transplantation; very shortly the T. Cruzi will be invading the heart silograft.

Several researchers have developed devices for long term treatment of CHF. Thus, Pierce et al have disclosed a DC brushless motor-driven total artificial heart.

Portner & associates have developed an electrically powered solenoid energy converter coupled to a dual pusher-plate sac type blood pump.

A belt skin transformer providing transmission of primary power across the intact skin during a short period of time.

White tested thermal powered systems comprised by a stirling engine/hydraulic converter attached to a ventricular assisting device.

Liotta et al used a DC brushless motor-driven single pusher plate at an animal laboratory at the early days of artificial heart research; etc.

The disadvantage common to these devices is the need of requiring a power source external to the body, through a percutaneous access port.

The life quality is severely restricted and patients are subject to serious complications, such as infections.

Further, the transmission of electrical power through intact skin requires permanent care of the recharging of internal batteries.

Works on remodelling the outstanding properties of skeletal muscle plasticity have lead cardiomyoplasty to treat CHF in man.

The pacing of skeletal muscle grafts with a train of pulses from a muscle stimulator may transform a high power but fatigable skeletal muscle into a somewhat lower power but fatigue-resistant muscle which matches cardiac muscle's work output on a gram-per-gram basis.

Further, the concept of using the autologous skeletal muscle for cardiac assistance is not new, although former attempts had characteristics and features different from those of the instant invention.

In this respect, the first documented attempt was disclosed by Adrian Kantrowitz. Kantrowitz wrapped the left hemidiaphargm of a dog to a segment of the descending thoracic aorta and stimulated diaphragm contraction during diastole.

Apart from dynamic cardiomyoplasty, Stephenson et al reported on the use of muscle energy as an aid in blood pumping. Thus, the Latissimus dorsi muscle is detached from all of its insertion and is wrapped around a conical mandrel to create a ventricular-like shaped skeletal muscle pouch.

Furthermore, Chiu et al have developed a skeletal muscle-powered implantable chamber counterpulsator.

Liotta et al have reported the concept of the advantages of the natural linear contraction of the skeletal muscle thus avoiding a major anatomical disruption.

Spitzer proposed the lower insertion of the rectus femoris muscle and attachment thereto to a 200 ml piston implanted in the thigh.

Contraction of the rectus femoris muscle creates physiological pressures capable of driving an artificial heart in the chest.

Ugolini reported that a fluid energy collector should be capable of storing energy from the contraction of the psoas major muscle and transferring it by a hydraulic conduit to an artificial heart pump.

Farrar and Hill disclosed a muscle-powered two-stage mechanical to hydraulic energy convector which could be applied to a circulatory blood pump.

At the animal laboratory (dogs and calves), Ltotta et al reported on physiological studies concerning the linear-pull force and displacement of the LD muscle.

An endogenous source of power employing skeletal muscle for cardiac aid devices is of great advantage. Problems related to the use energizing systems (electrical, pneumatic, hydraulic) outside the body are thus avoided.

SUMMARY OF THE INVENTION

The instant invention proposes to use the mechanical force of the Latiesimus dorsi muscle in its linear pull for maximum efficiency.

The surgical process, which will be described in detail hereinbelow, only detaches the humeral insertion of the Latissimus dorsi muscle. This avoids a major disruptive dissection severely comprising the major source of its vascular supply, as seen in both cardiomyoplasty and in the creation of skeletal muscle ventricular-like pouches.

Therefore, the muscle-powered assisting device proposed by the instant invention is highly reliable due to its simplicity.

A strong cable connects the muscle-mechanical coupling, the force multiplicator, and the lever actuator system of the dual pusher-plate blood pump.

Further, in the instant invention, an external hydraulic system is only used to start the blood pumping during surgery and as a stand-by backup during the immediate post-operative period.

Research work for the instant invention began with the search of a mechanical-to-hydraulic energy converter. This approach was abandoned since hydraulic systems are not safe for long term use, mainly due to fatigue or rupture of moving parts.

Therefore, the implantable mechanical system for assisting blood circulation uses a blood circulation pump (a), and is characterized by, being actuated by the power produced by the linear contraction of the skeletal muscle (15), comprising for its two-phase application: a combined prosthesis defining the bio-mechanical coupling (1) between said skeletal muscle (15) and the implantable mechanical system; a muscle action force multiplier (c) transmitting force through a lever system (23) driving compression plates of the blood chamber formed into the pump (a); said biomechanical coupling (1), the force multiplier (c) and the lever system (23) forming a functional unit interconnected by means of lead wires, and mechanically by means transmiting movement; the system further comprising a means (b) for measuring force and the displacement of the skeletal muscle (15) driving the pump (a), during the electro-stimulation period through the system.

BRIEF DESCRIPTION OF THE DRAWINGS

In the figures, the same reference numerals designate the same or equivalent parts, the assembly of several elements being designated by letters.

References are according to the following detail:
(a) assisted blood circulation pump
(b) force cell (for measuring the force and displacement of the skeletal muscle)
(b') double Joint sub-assembly
(c) sub-assembly multiplying muscle force
(d) connecting assembly between (15) and (6)
(1) biomechanical coupling
(2) permanent plastic sheath
(3) coating elastic tube
(4) simple joint
(5) secondary plastic sheath
(6) force multiplier box
(6') cover for (6)
(7) intraventricular connector
(8) ventricle apex prosthesis
(9) percutaneous button
(10) external auxiliary system
(11) pump body
(11')ports connecting to blood channeling
(12) compensating bladder (or blister)
(13) electrodes
(14) programmable cardiomyostimulator
(15) mass of Latissimus dorsi muscle (skeletal muscle)
(16) capsule of (b)
(16')joint of (b')
(17) sensor electrode
(18) larger spring of (b)
(19) smaller spring of (b)
(20) pulleys
(21) anti-friction washer
(22) pulley shaft with bearing
(28) levers
(24) flexible straps or bands
(25) transmission chain
(26) toothed wheels (or gears)
(30) inlet control of power source outside the body
(31) external power system (in the embodiment shown, extracorporeal piston with hydraulic cylinder).

DETAILED DESCRIPTION OF THE INVENTION

Figure 1:
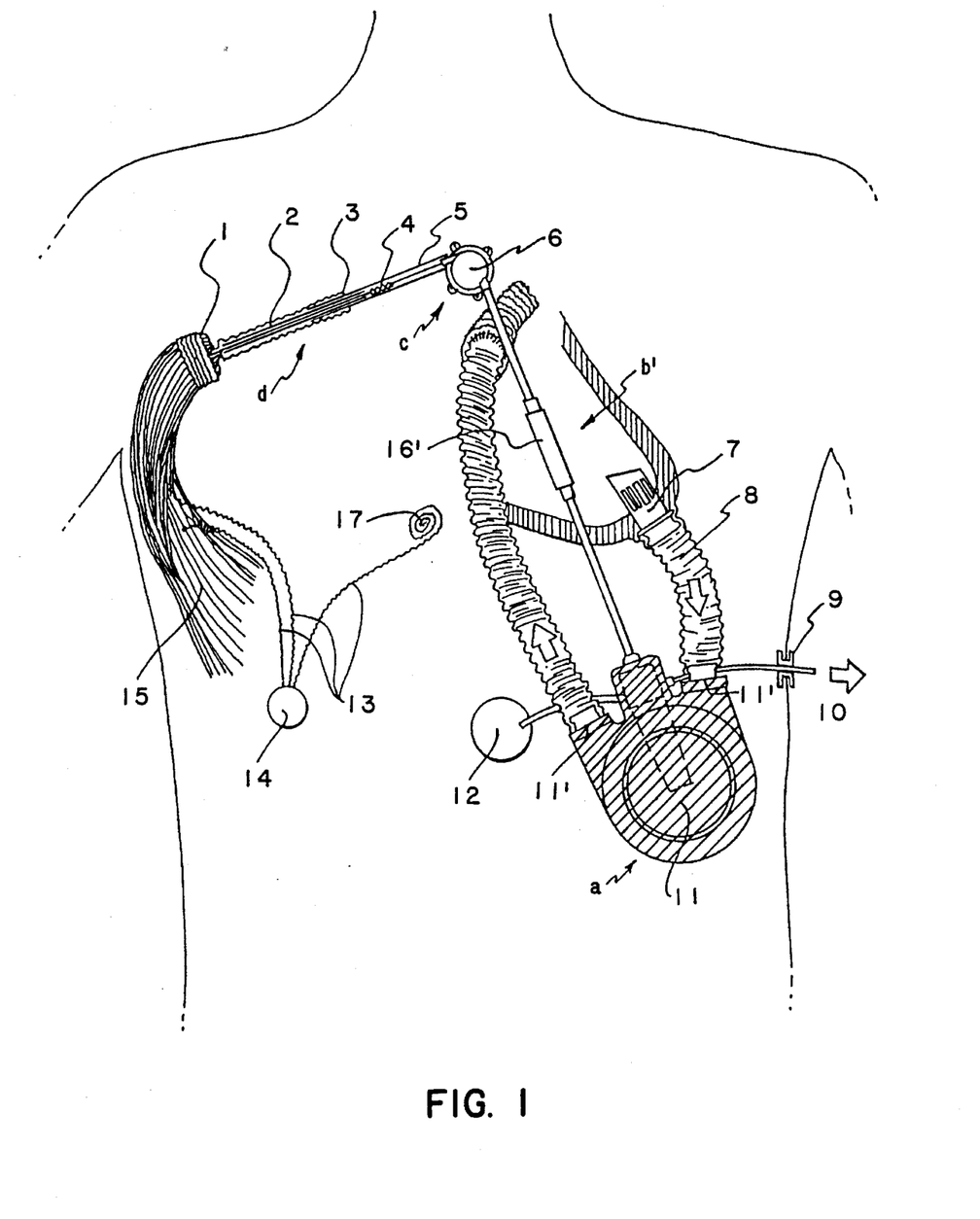
FIG. 1 is a schematic view showing the mechanical system implanted into the body, with it general constitution and different forming elements.

As indicated above, the invention refers to a mechanical system for implantation into the body—in humans and animals—for assisted blood circulation and essentially, as shown in the drawings, comprises the combination of the following constituting elements to the ends indicated hereinbelow:

1. Bio-mechanical coupling (1). The prosthesis was prepared to be used as a Joint (d) between the muscle (15) tendon and the mechanical system (FIG. 1). Thus, the linear pull force of a skeletal muscle (15) is used as power source for a permanent implantation of a blood pump (a). In practice, a special tapered graft was developed, according to two principles: the graft is made of surgical dacron cloth, the inner part of which—of the velour type—is highly porous and favors a deep penetration of tissues during the muscle (15) healing process; the outer portion is a TEFLON-like surface for preventing any impairment of translational movements of the bio-mechanical coupling (1).

Further, a titanium machined piece is incorporated to the combined graft, thus constituting a solid anchor for the tension cable.

2. Cell (b) measuring the force and displacement of the muscle (15) during the electric stimulation training period thereof, which lasts from 6 to 12 weeks. This cell was designed in different models and, the simplest one (FIG. 2) comprises a capsule (16) housing several springs (18) and (19) having different tension between each other, as well as a sensor electrode (17).

Figure 2:
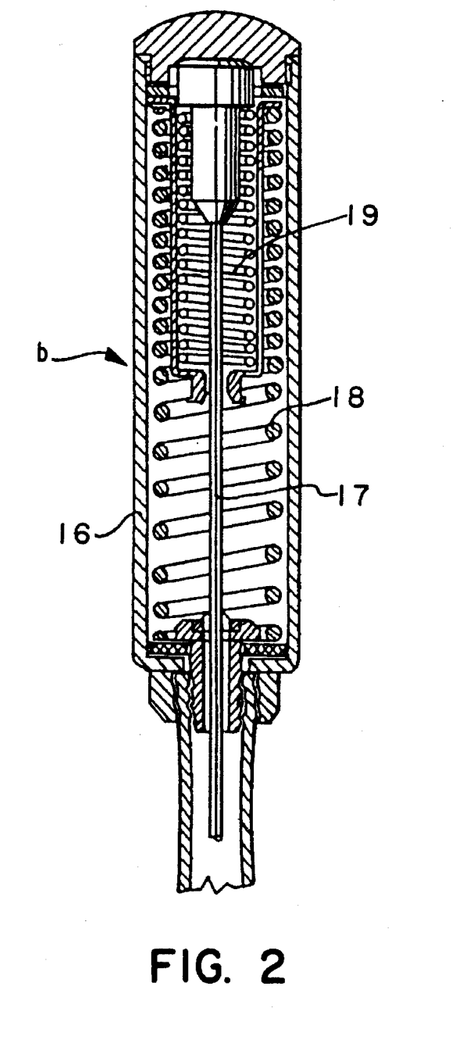
FIG. 2 is a longitudinal detailed section of the force and displacement cell for measuring the electrical transformation of the skeletal muscle.

In the experiences carried out, the simplest and most practical force cell (b) used measures force and displacement during transformation of the LD muscle (15).

At the beginning of the muscle training (first spring (19)), the loading force acts from 0 to 800 g with 2,5 cm of displacement. The second spring (18) acts from 800 g to 1.6 kg, with 1 cm displacement (FIG. 2); a third spring may exist acting from 1.6 kg with 1 cm displacement.

Displacement is measured by means of ecographs as well as of X-ray image.

A much more complex 10 mm diameter chamber was designed: the camber has a 3–12 V, CC, 100 mW engine. The engine controls displacement of the springs; the force is measured with a strain gage applied on a flexible metal disc. Force and displacement parameters are controlled from outside, by means of percutaneous cables as well as by telemetry.

Figures 6, 6A:
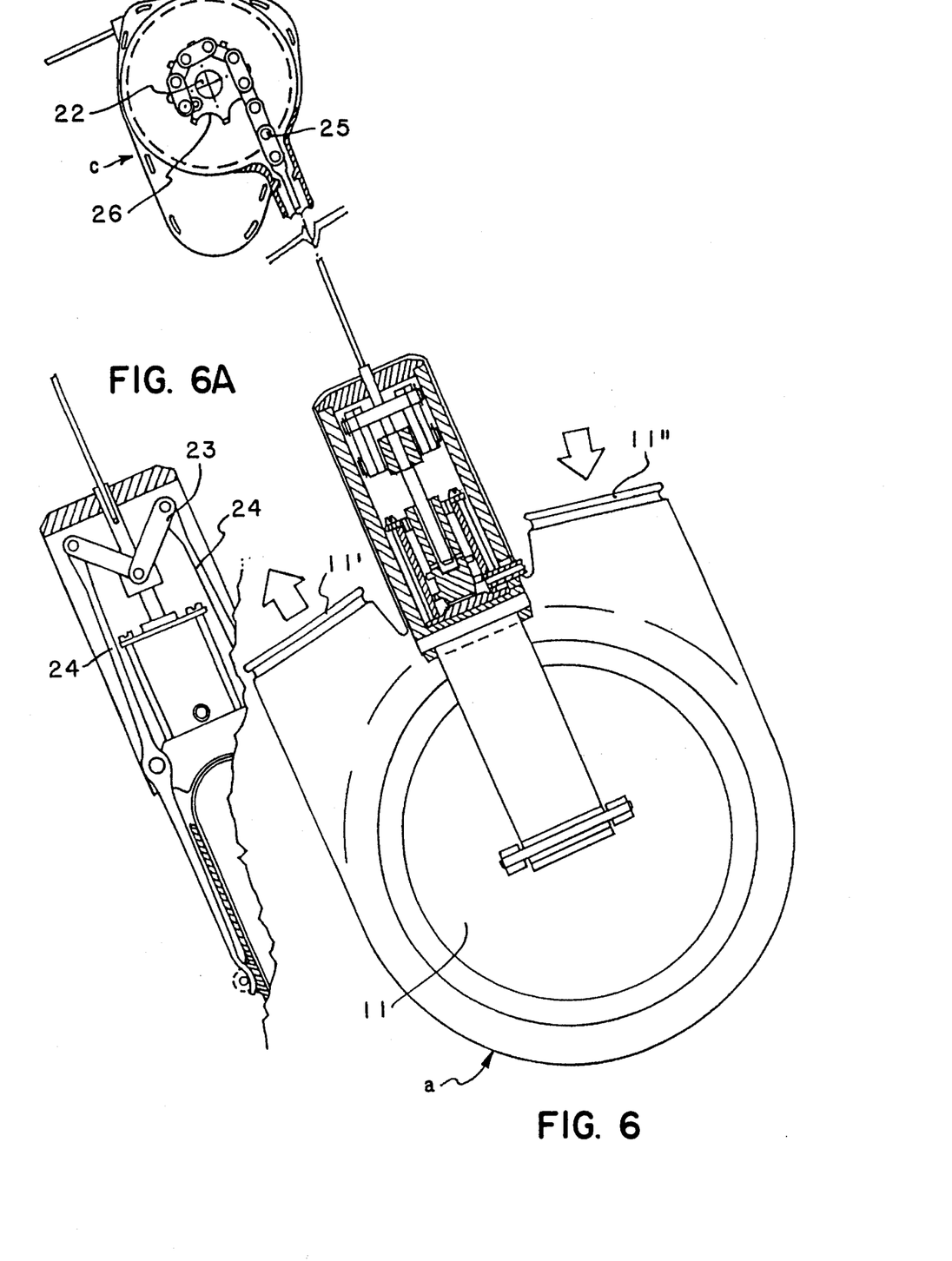
FIG. 6 is a schematic detailed section of the multiplier, in another embodiment using gears and chains; further showing the way in which such forces are transmitted to the blood chamber of the pump.
FIG. 6a is a detail of the device of FIG. 6, using flexible bands (strips).

3. The muscle (15) force multiplier, forming part of a multiplier sub-assembly (c), as shown in FIG. 1, interposes at a point of the cable travel, sheathed into the plastic sheath (2), with a coating elastic tube (3) and a simple joint (4) at the inlet of box (6). Different models of this multiplier (c) have been designed for increasing the mechanical power, namely, connection of two or three different diameter pulleys (20) Joined by a flexible cable (FIGS. 1 and 3); or connection of two or more gears (26) attached to a rack or chain (25) to carry out their specific function (FIG. 6).

Figure 3:
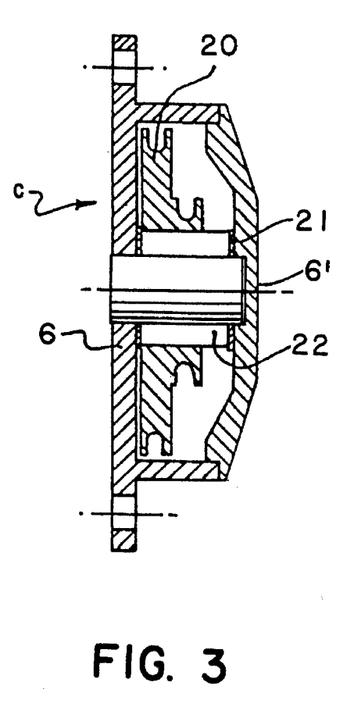
FIG. 3 is a diametral section of the pulley set used for transmitting force by means of cables.

The basic concept is to increase muscle force. For example, from a maximum muscle force of 4 kg and 3 cm of displacement, multiplier (c) increases this force to 12 kg and decreases the displacement to 1 cm.

4. The lever system (23) which, as mentioned, operates the pump (a). These levers were designed in several models, for example: a wedge with edges pre-fixed in curved figures sliding between two rollers end which, upon being tensioned by muscle contraction imparts a predetermined systolic movement to compression plates.

Figures 7, 8, 9:
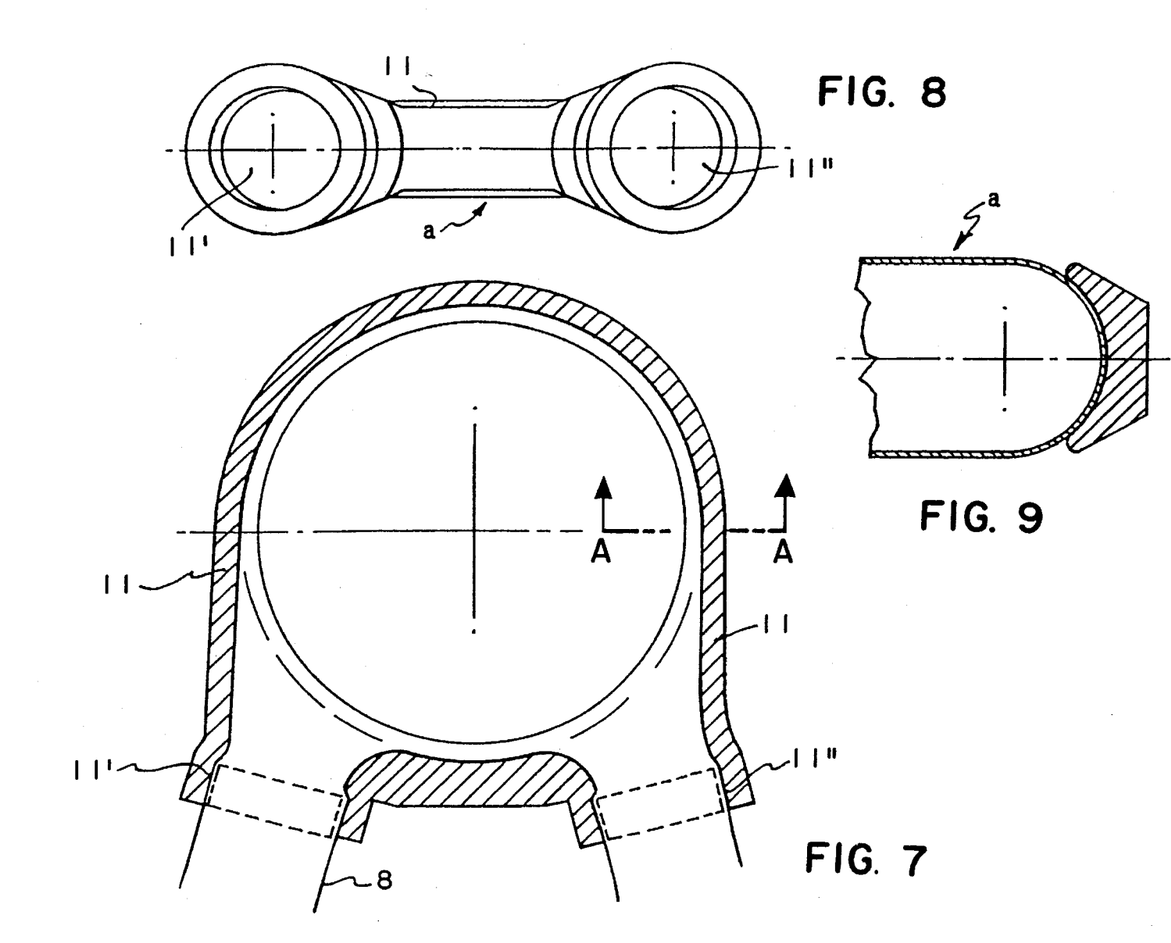
FIG. 7 is a cross-section of the pump body.
FIG. 8 is a front view of the pump shown as from its ports coupling to the blood channeling lines.
FIG. 9 is a cross detailed section of the same pump body, with a planer region for supporting the nippers (pliers).

5. The blood chamber (FIGS. 6 to 8) which, provided with two compressing plates, is comprised by the pump (a) body (11) having ports (11') connected to the heart by conduits; (8) designates the ventricular apex prosthesis.

The blood pumping system is thus formed by the driving levers system (23), which by two metal straps or flexible straps (24), FIG. 6-A, connect to a hydraulic piston and to the blood chamber of pump (a); the latter being made of polyurethane.

Figure 5:
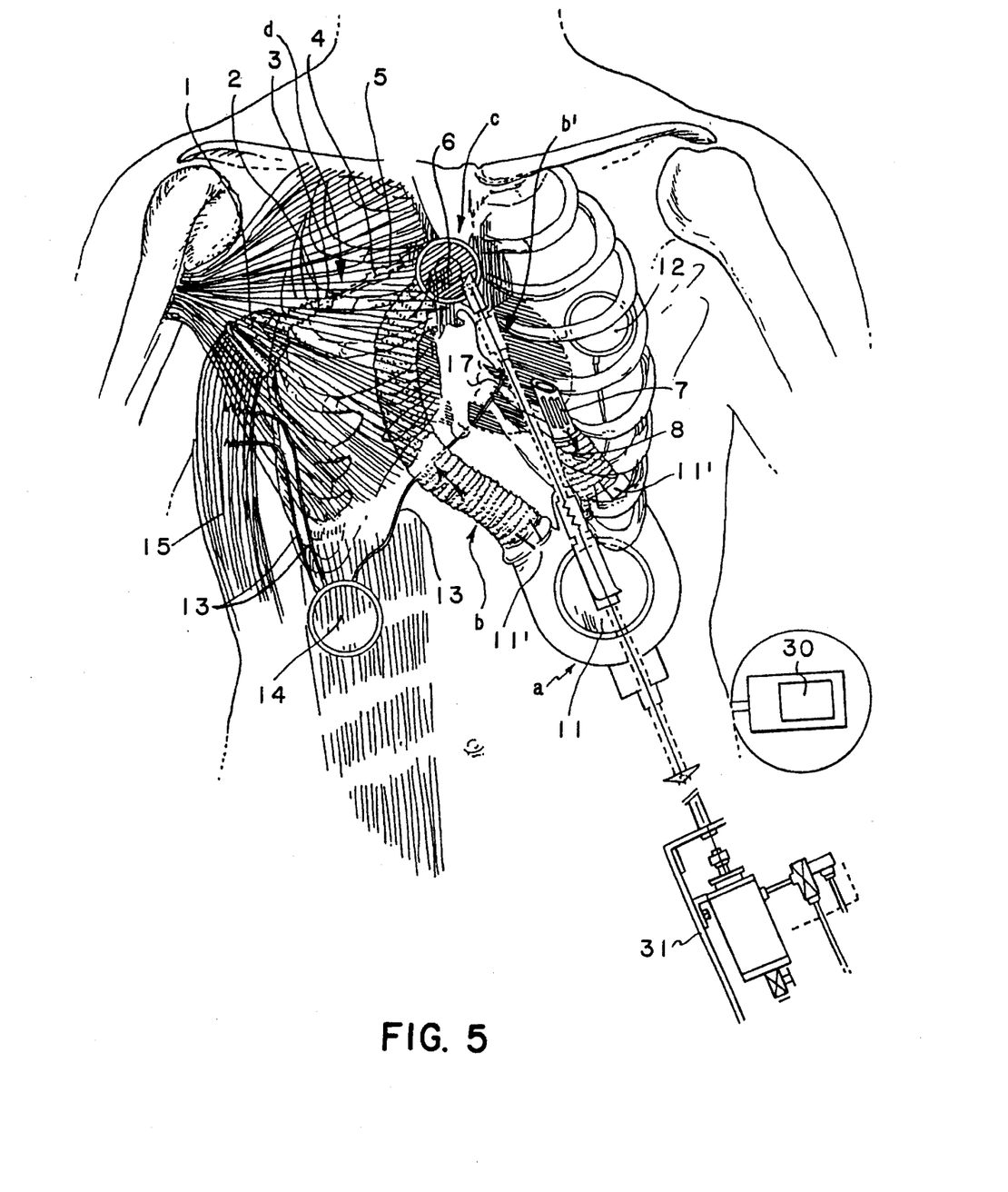
FIG. 5 is another schematic view of phase II of the implanted system.

Therefore, such a system converts hydraulic force into mechanical force, while the mentioned hydraulic piston of pump (a) is powered by a hydraulic force generated by an outer power system (31), formed by a piston slidingly contained into an extracorporeal hydraulic cylinder, with which it communicates through an access or percutaneous button (9), FIGS. 1 and 5.

The external system starts blood pumping during surgery, and is prepared, if required, to be used during the immediate post-operative period.

Electrical remodelling, force and displacement of the LD muscle (15) are closely monitored during the preparation period (I).

6. The highly flexible steel cable or lead wire, transmitting muscle force and displacement to the lever system (23) which, connected at (16') actuate the cited blood chamber of pump (a).

It is to be noted that the bio-mechanical coupling (1) prosthesis, the force multiplier sub-assembly (c), and the system of driving levers (23) form a functional unit due to a cable and lead wires system.

Further, as may be understood, in the assembly disclosed there are other component end auxiliary elements such as, for example, the compensating bladder (12) subassembly, end other unsubstituting elements such as the cardiomyostimulator, which are not detailed herein since they are not basic aspects of the invention.

GENERAL DESCRIPTION OF THE SURGICAL PROCESS

In the instant invention, the muscle-powered ventricular assistance device (15) is proposed to be a two-stage procedure.

During Phase I, 6 to 12 weeks, the LD muscle is transformed by means of a continued electrical stimulus.

Further, the muscle (15) force and its displacement are closely monitored, and from 24–48 hours after surgery the patient is discharged from hospital.

However, severely ill patients may require cardiac assistance immediately. Then, the procedure should be reversed; the circulatory blood pump with an external power source is implanted first. In this case, the patient should remain at the medical center 8 to 12 weeks, time insumed by the electrical preconditioning of the muscle. In this case, costs would increase notably.

The steps or phases for applying the invention are as follows:

PHASE I

Figure 4:
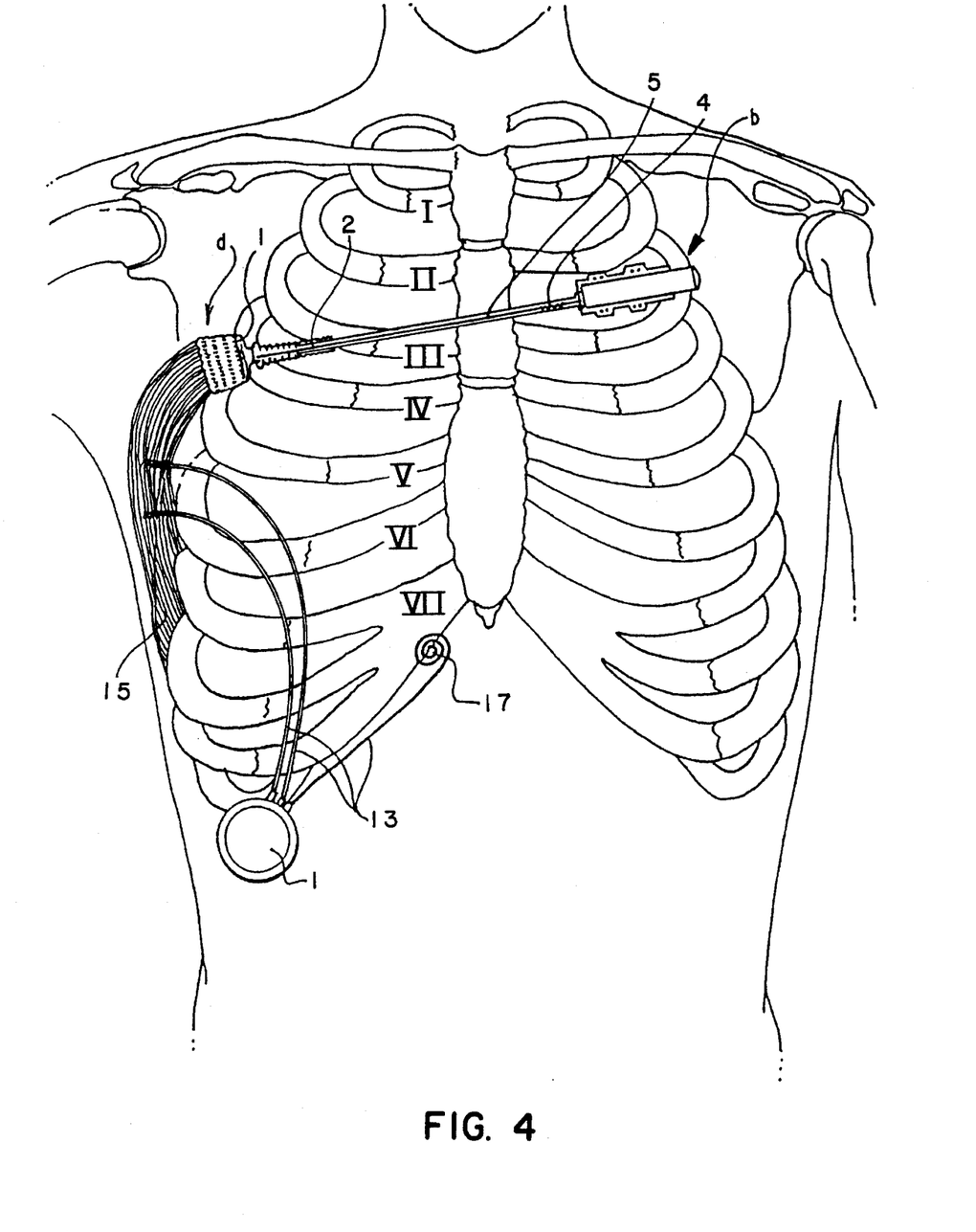
FIG. 4 is a schematic view of phase I of the invention showing the electrical pre-conditioning of the skeletal muscle employed.

Electrical preconditioning of LD muscle (15) (FIG. 4)

1. The humeral insertion of the right LD muscle (15) is surgically taken down in a block, including a longitudinal segment of bone and periostium.

The skin incision is made from a point higher than 1–2 cm from the humeral insertion of the LD muscle; the incision extends downwards to about the seventh rib. The vertical incision follows the rear auxiliary line at the anterior edge of the LD muscle.

The patient is in supine position and is anesthetized without curariform drugs.

The muscle tension force (passive stretching force) is measured with a dynamometer. The tendon of the LD muscle (15) is pulled to the point of normal humeral insertion. This measure is the normal passive stretching force or diastolic force, this last denomination for homologation with Frank-Starling heart law.

2. The LD muscle (15) neurovascular bundle is exposed.

3. A pair of intramuscular electrode leads (13) are inserted. The proximal cathode lead is woven near the thoracodorsal nerve branches; the anode lead is located 6–8 cm spaced apart in the mass of LD muscle (15). An analyzer is used for measuring acute threshold and the resistance of the muscle and the leads. The muscle stimulator is implanted in the sheath of the right abdominal rectus muscle. The epimyocardiac sensing electrode is left close to the sternal midlines thus it is prepared for Phase II (FIG. 1).

4. Bio-mechanical coupling is completed.

5. Cell (b), for measuring the force and displacement during the electrical preconditioning period (between 6 and 12 weeks) is placed to the left in the intercostal space between the second (II) and the third (III) ribs.

6. The tension cable coated by a TEFLON lead (3) of 3 mm inside diameter, is passed from the right area of the serratus major muscle to reach the cell (b) implanted at the left chest wall. A simple tubular instrument is used to pass the tension cable from the right anterior auxiliary line to the anterior left pectoral muscle area.

Post-operative Studies in Phase I (8–10 weeks)

Phase I is the most important step in the entire methodological conception of the proposed system.

During phase I, the right LD muscle (15) is preconditioned (trained); but, from a practical viewpoint, the most significant feature is that the force and displacement of the LD muscle (15) are monitored to search for the right time to move to Phase II.

Furthermore, during Phase I cicatrization (healing) of biological (LD muscle tendon) and mechanical interfaces takes place.

When the LD muscle (15) is stimulated, the progressive movement of the bio-mechanical coupling (1) creates a natural sliding sheath on the right serratus major muscle which prevents unimpeded translational movement of the tendon and its mechanical coupling.

PHASE II (FIG. 5)

1. LD muscle (15) training cell (b) is removed.

2. Median sternotomy is performed; care is taken to avoid injury to the teflon conduit (3 mm ID) crossing the midline subcutaneously.

3. A 20 mm low porosity woven dacron graft is sutured to the ascending aorta.

4. The patient may be placed on extracorporeal circulation to safely perform the insertion and suture fixation of the left intraventricular connector through the LV apex (FIG. 2).

5. A digital passage is prepared, from the LV apex area through the costo-diaphragmatic angle to reach the pre-peritoneal abdominal space in order to allow the easy passage of the intraventricular inlet pump connector.

6. The left intraventricular connector is secured to the inlet connector of the blood pump (a).

7. The 20 mm low porosity dacron graft is secured to the outlet connector of the blood pump (a).

8. The LVAD pumping mechanism is activated with the auxiliary external power system (S1). The patient is gently weaning from the extracorporeal circulation.

Two external power systems have been developed: a mechanical system and a hydraulic system.

The external line is connected through a percutaneous access port or button (9), distant from the surgical area.

The external driving LVAD system is used temporarily and remains on stand-by during the immediate postoperative period.

The power and displacement of the LD muscle (15) are monitored closely.

9. The sensing lead of the cardio-myostimulator, which remained prepared adjacent the sternal midline in Phase I, is implanted in the epimyocardium.

It is obvious that, upon practicing the invention, those skilled in the art may introduce modifications in what concerns to certain details of construction and shape, without departing from the basic principle thereof, which are only limited by the spirit and scope of the following claims.

I claim:

1. An implantable mechanical system for assisting blood circulation, wherein the system is adapted to be actuated by power produced by linear contraction of a skeletal muscle, comprising:

a blood circulation pump comprising a blood chamber and compression plates;

a lever system means for driving said compression plates;

a muscle action force multiplier means for transmitting a multiplied force through said lever system means and driving said compression plates;

a prosthesis defining a biomechanical coupling between said skeletal muscle and said force multiplier; and means for measuring force from said skeletal muscle and displacement of said skeletal muscle while driving said pump during an electro-stimulation period used with the system;

wherein said prosthesis, said force multiplier means, and said lever system means form a functional unit mechanically interconnected by lead wires which transmit movement and force through said unit.

2. The system according to claim 1, wherein said lever system means is connected to a hydraulic piston.

3. The system according to claim 2, further comprising a second extracorporeal piston, wherein said hydraulic piston is implantable and is adapted to be driven by said second extracorporeal piston, said hydraulic piston and said extracorporeal piston comprising a portion of a hydraulic circuit which further includes a conduit adapted to pass through a percutaneous access.

4. The system according to claim 1, wherein said means for measuring force and displacement comprises an implantable cell containing working springs.

5. The system according to claim 4, wherein said cell includes an outer spring and an inner spring wherein said outer spring is designed to displace at a higher loading force than said inner spring.

6. The system according to claim 1, wherein the muscle force multiplier means is positioned between said prosthesis and said lever system means which drives said blood pump and further comprises a pulley set for guiding said lead wires.

7. The system according to claim 6, wherein the pulley set is are comprised of at least two adjacent and connected pulleys having a common axis, wherein the diameter of one of the two pulleys is larger than the diameter of another of the two pulleys so as to achieve force multiplication when a force is applied to the pulley having the larger diameter.

8. The system according to claim 1, wherein the muscle force multiplier means is positioned between said prosthesis and said lever system which drives said blood pump and further comprises gear sets controlled by racks.

9. The system according to claim 1, wherein:

said lever system means comprises two levers for transmitting forces wherein each of said two levers has an end connected to said force multiplier means and an opposite end connected to one of said compression plates via flexible straps; and said pump includes inlet and outlet ports connected to corresponding conduits which are adapted to channel blood from a heart cavity to an arterial circulation system.

10. The system according to claim 1, wherein said lead wires extend between said biomechanical coupling and said force multiplier and said lead wires extend between said force multiplier and said lever system.

11. The system according to claim 1, wherein said lever system and said force multiplier are separate and distinct elements attached by said lead wires.

* * * * *